(12) United States Patent
Takano et al.

(10) Patent No.: US 8,148,348 B2
(45) Date of Patent: Apr. 3, 2012

(54) METHOD OF STABILIZING S-ADENOSYL-L-METHIONINE AND STABILIZED COMPOSITION

(75) Inventors: Kentarou Takano, Niigata (JP); Shinyo Gayama, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 551 days.

(21) Appl. No.: 12/161,030

(22) PCT Filed: Jan. 16, 2007

(86) PCT No.: PCT/JP2007/050514
§ 371 (c)(1),
(2), (4) Date: Jul. 16, 2008

(87) PCT Pub. No.: WO2007/083631
PCT Pub. Date: Jul. 26, 2007

(65) Prior Publication Data
US 2010/0168048 A1    Jul. 1, 2010

(30) Foreign Application Priority Data
Jan. 17, 2006   (JP) .................................. 2006-008884

(51) Int. Cl.
*A61K 31/7076* (2006.01)
*A61K 31/341* (2006.01)
*A61K 31/10* (2006.01)

(52) U.S. Cl. ............................ 514/46; 514/474; 514/709

(58) Field of Classification Search .................... 514/46, 514/474, 709
See application file for complete search history.

(56) References Cited

U.S. PATENT DOCUMENTS
3,954,726 A    5/1976   Fiecchi
4,621,056 A *  11/1986  Gennari ........................ 435/85
5,128,249 A *  7/1992   Gennari ........................ 435/113
2002/0188116 A1   12/2002  Deshpande et al.
2003/0032796 A1*  2/2003   Deshpande et al. ....... 536/27.31

FOREIGN PATENT DOCUMENTS

| | | |
|---|---|---|
| EP | 0 072 980 | 3/1983 |
| EP | 0 141 914 | 5/1985 |
| EP | 0 162 323 | 11/1985 |
| EP | 0 189 322 | 7/1986 |
| EP | 1 091 001 A1 | 4/2001 |
| FR | 2275220 | 1/1976 |
| JP | 52-048691 | 4/1977 |
| JP | 57-156500 | 9/1982 |
| JP | 59-051213 | 3/1984 |
| JP | 59-139320 | 8/1984 |
| JP | 61-227792 | 10/1986 |
| JP | 64-049274 | 2/1989 |
| JP | 01-049275 | 10/1989 |
| JP | 04-021478 | 4/1992 |
| JP | 06-030607 | 4/1994 |
| WO | WO 89/03389 | 4/1989 |

OTHER PUBLICATIONS

Machine translation of FR 2275220, European Patent Office, http://epo.worldlingo.com/, accessed online on Aug. 30, 2010.*
Definition of derivative, Oxford English Dictionary, http://dictionary.oed.com, accessed online on May 20, 2010.*
Extended European Search Report, including Supplementary European Search Report and European Search Opinion, dated Jan. 15, 2010, for Application No. EP 07 70 6841.

* cited by examiner

*Primary Examiner* — Shaojia Anna Jiang
*Assistant Examiner* — Jonathan S Lau
(74) *Attorney, Agent, or Firm* — Antonelli, Terry, Stout & Kraus, LLP.

(57) ABSTRACT

Provided are a process for producing a S-adenosyl-L-methionine-containing composition which is very excellent in a stability by adding at least ascorbic acids or salts thereof to a composition liquid containing S-adenosyl-L-methionine and then drying the above composition liquid or separating and drying a crystallized deposit obtained from the above composition liquid, a S-adenosyl-L-methionine-containing composition obtained by the above production process and a molding obtained from the above composition.

5 Claims, No Drawings

METHOD OF STABILIZING S-ADENOSYL-L-METHIONINE AND STABILIZED COMPOSITION

BACKGROUND OF THE INVENTION

The present invention relates to a stabilizing method for S-adenosyl-L-methionine (hereinafter referred to as SAMe) and a composition containing SAMe stabilized by the above method.

More specifically, the present invention relates to a production process for a SAMe-containing composition which is excellent in a storage stability, characterized by adding at least ascorbic acids or salts thereof to a composition liquid containing SAMe and then drying the above composition liquid or separating and drying a crystallized deposit obtained from the above composition liquid, a SAMe-containing composition obtained by the above production process and a molding prepared by using the above composition.

SAMe is a water-soluble physiologically active substance which plays an important role as a methyl group donor in methylation carried out by various transmethylases in a living body. It is observed in almost all cells of a human body and acts as a cofactor in various biochemical reactions, and it is an indispensable substance for maintaining cartilages and producing compounds in the brain.

As described above, SAMe is an important water-soluble physiologically active substance and is widely used as a therapeutic medicine for depression, liver disease, arthritis and a functional food in the West.

RELATED ART

Accordingly, SAMe is strongly required to be produced by a simple and economical process and supplied to the market, but SAMe has the property that it is thermally instable and readily decomposed, and therefore a lot of trials has been made as a countermeasure thereof for the purpose of enhancing the storage stability.

In general, processes which have so far been used as a production process for SAMe include a process in which a culture medium containing L-methionine as a precursor is used to produce SAMe by fermentation (refer to, for example, patent documents 7 to 9 and non-patent documents 1 to 5, 8 and 9), a process in which a SAMe synthetic enzyme (methionine adenosyl transferase) isolated and refined from microorganisms such as yeasts is used to produce enzymatically SAMe using adenosine 5'-triphosphate (ATP) and L-methionine as a substrate (refer to, for example, a patent document 1 and non-patent documents 6, 7 and 9 to 12) and a process in which compositions of SAMe obtained by processes (refer to, for example, a patent document 10 and a non-patent document 11) according to a synthetic process are refined by chromatography and the like and converted into salts with sulfuric acid and p-toluenesulfonic acid or salts with butanedisulfonic acid to thereby stabilize SAMe (refer to, for example, patent documents 2 to 9).

However, a period in which even the SAMe salts prepared by the processes described above can relatively stably be stored is as short as about one month in an acceleration test at 40° C. and a humidity of 75%, and therefore a production process for a SAMe-containing composition which can stably be stored over a longer period of time, a SAMe-containing composition obtained by the above production process and a molding prepared by using the above composition have strongly been desired to be provided.

Patent document 1: Japanese Patent Publication No. 227792/1986
Patent document 2: Japanese Patent Application Laid-Open No. 51213/1984
Patent document 3: Japanese Patent Application Laid-Open No. 48691/1977
Patent document 4: Japanese Patent Application Laid-Open No. 49274/1989
Patent document 5: Japanese Patent Publication No. 49275/1989
Patent document 6: Japanese Patent Publication No. 501970/1991
Patent document 7: Japanese Patent Publication No. 21478/1992
Patent document 8: Japanese Patent Publication No. 30607/1994
Patent document 9: European Patent Application Laid-Open No. 1091001
Patent document 10: U.S. Patent Application Laid-Open No. 2002/0188116
Non-patent document 1: Schlenk F., DePalma R. E., J. Biol. Chem., 229, p. 1037 to 1050 (1957)
Non-patent document 2: Shiozaki S., et al., Agric. Biol. Cem., 53, p. 3269 to 3274 (1989)
Non-patent document 3: Schlenk F., DePalma R. E., J. Biol. Chem., 229, p. 1051 to 1057 (1957)
Non-patent document 4: Kusakabe H., Kuninaka A., Yoshino H, Agric. Biol. Cem., 38, p. 1669 to 1672 (1974)
Non-patent document 5: Mudd S H., Cantoni G L., et al., J. Biol. Chem., 231, p. 481 to 492 (1958)
Non-patent document 6: Markham G. D., et al., J. Biol. Chem., 225, p. 9082 to 9092 (1980)
Non-patent document 7: Markham D. J, DeParisis J., J. Biol. Chem., 259, p. 14505 to 14507 (1984)
Non-patent document 8: Shiozaki S., et al., J. Biotechnology., 4, p. 345 to 354 (1986)
Non-patent document 9: Thomas D., Surdin-Kerjan Y., J. Biol. Chem., 262, p. 16704 to 16709 (1987)
Non-patent document 10: Thomas D., Cherest H., et al., Mol. Cell. Biol., 8, p. 5132 to 5139 (1988)
Non-patent document 11: Jose R. Mator, Frank M. Raushel, Chi-Huey Wong., Biotechnology and Applied Biochemistry., 9, p. 39 to 52 (1987)
Non-patent document 12: Jeongho Park, Junzhe Tai, Charles A. Roessner and A. Ian Scott., Bioorganic & Medical Chemistry, Vol. 4, No. 12, p. 2179 to 2185 (1996)

DISCLOSURE OF THE INVENTION

A composition of SAMe produced by a conventional process has room for further improvement in a stability thereof and can not sufficiently be satisfied.

That is, an object achieved by the present invention is to establish a production process in which a SAMe-containing composition having more excellent stability than ever is obtained in a simple manner and provide a SAMe-containing composition obtained by the above production process and a molding prepared by using the above composition.

Intensive researches repeated by the present inventors in order to achieve the object described above have resulted in finding that a SAMe-containing composition can be improved in a stability to a large extent by employing a process in which at least ascorbic acids or salts thereof are added to a composition liquid containing SAMe and in which a solvent contained in the above composition liquid is then removed by distillation to dry the composition liquid or a process in which a solvent is added to the above composition liquid as it is or after subjected to refining and concentrating operations to crystallize the SAMe-containing composition and in which a deposit thus obtained is separated and dried, and thus the present inventors have come to complete the present invention.

That is, the present invention relates to a production process for a SAMe-containing composition which is excellent in a storage stability, a SAMe-containing composition obtained by the above production process and a molding prepared by using the above composition, and they are shown in the following items (1) to (11).

(1) A production process for a S-adenosyl-L-methionine-containing composition, comprising adding at least ascorbic acids or salts thereof to a composition liquid containing S-adenosyl-L-methionine and then drying the above composition liquid or separating and drying a crystallized deposit obtained from the above composition liquid.

(2) The production process for a S-adenosyl-L-methionine-containing composition as described in the above item (1), wherein sulfuric acid or a salt thereof and the ascorbic acids or the salts thereof are added to the composition liquid containing S-adenosyl-L-methionine, and then the above composition liquid is dried or a crystallized deposit obtained from the above composition liquid is separated and dried.

(3) The production process for a S-adenosyl-L-methionine-containing composition as described in the above item (1), wherein p-toluenesulfonic acid or a salt thereof and the ascorbic acids or the salts thereof are added to the composition liquid containing S-adenosyl-L-methionine, and then the above composition liquid is dried or a crystallized deposit obtained from the above composition liquid is separated and dried.

(4) The production process for a S-adenosyl-L-methionine-containing composition as described in the above item (1), wherein sulfuric acid or a salt thereof, p-toluenesulfonic acid or a salt thereof and the ascorbic acids or the salts thereof are added to the composition liquid containing S-adenosyl-L-methionine, and then the above composition liquid is dried or a crystallized deposit obtained from the above composition liquid is separated and dried.

(5) The production process for a S-adenosyl-L-methionine-containing composition as described in the above item (2) or (4), wherein an amount ratio of sulfuric acid or the salt thereof to S-adenosyl-L-methionine contained in the S-adenosyl-L-methionine-containing composition obtained falls in a range of 0.1 to 3 time mole.

(6) The production process for a S-adenosyl-L-methionine-containing composition as described in the above item (3) or (4), wherein an amount ratio of p-toluenesulfonic acid or the salt thereof to S-adenosyl-L-methionine contained in the S-adenosyl-L-methionine-containing composition obtained falls in a range of 0.1 to 2 time mole.

(7) The production process for a S-adenosyl-L-methionine-containing composition as described in any of the above items (1) to (6), wherein an amount ratio of the ascorbic acids or the salts thereof to S-adenosyl-L-methionine contained in the S-adenosyl-L-methionine-containing composition obtained falls in a range of 0.1 to 2 time mole.

(8) The production process for a S-adenosyl-L-methionine-containing composition as described in the above item (1), wherein the ascorbic acids are ascorbic acid or ascorbic acid derivatives.

(9) The production process for a S-adenosyl-L-methionine-containing composition as described in the above item (8), wherein the ascorbic acid derivative is 2-glucoside ascorbate, phosphoric acid ascorbate, palmitic acid ascorbate or stearic acid ascorbate.

(10) A S-adenosyl-L-methionine-containing composition obtained by the production process as described in any of the above items (1) to (9).

(11) A molding prepared from the S-adenosyl-L-methionine-containing composition as obtained in the above item (10).

BEST MODE FOR CARRYING OUT THE INVENTION

SAMe used in producing the SAMe-containing composition of the present invention which is excellent in a storage stability shall not specifically be restricted in a production process thereof, and any of SAMe produced by fermentation using microorganisms, SAMe produced by a semisynthetic process using microbial enzyme and SAMe produced by a chemical synthetic process may be used.

These SAMe's may contain impurities in addition to SAMe, but it is a matter of course that SAMe which is subjected, if necessary, to refining operation before treated by the stabilizing method of the present invention is advantageously used since it can be applied to commercial products as it is.

The refining method includes various methods such as a chromatographic separating method carried out by using ion exchange chromatography, chelate resin chromatography and activated carbon chromatography, a fractional deposition method carried out by using a precipitant and an organic solvent, a membrane separating method carried out by using a reverse osmosis membrane and a UF membrane and a separating method carried out by using centrifugal separation and filtration, and refining may be carried out by any methods as long as they are methods by which refining can effectively be carried out.

A concentration of SAMe in the composition liquid containing SAMe is different according to a composition of a solvent contained therein, and it falls in a range of 5 to 25 mass %, preferably 10 to 20 mass % for drying the above composition liquid or separating and drying the crystallized deposit obtained.

The objects can sufficiently be achieved by using water as the solvent, and organic solvents such as acetone, ethanol and the like may be contained in water.

A pH of the composition liquid falls in a range of 1 to 5, preferably 1 to 4 from the viewpoint of a stability of SAMe.

If the pH is less than 1 or exceeds 5, a stability of SAMe in the composition liquid and a storage stability of the SAMe-containing composition obtained are reduced, and therefore it is not preferred.

The composition liquid containing SAMe can be controlled to the desired composition by subjecting the composition liquid to salt exchange carried out by contact treatment with a basic ion exchange resin of a proton acid type and dialytic treatment carried out by using an electrodialytic device and a reverse osmosis membrane.

An amount of the ascorbic acids or the salts thereof added to the composition liquid containing SAMe is added so that an amount ratio thereof to SAMe contained in the SAMe-containing composition obtained is 0.1 to 2 time mole, preferably 0.5 to 1.5 time mole.

If the mount ratio to SAMe is less than 0.1 time mole or exceeds 2 time mole, a storage stability of the SAMe-containing composition obtained is reduced.

In dissolving the ascorbic acids or the salts thereof, time required for dissolving them can be shortened by stirring.

The liquid temperature in dissolving is preferably as low as possible from the viewpoint of a stability of SAMe, and it falls in a range of usually 5 to 35° C., preferably 10 to 30° C. from the viewpoint of a solubility of SAMe.

The ascorbic acids or the salts thereof used in the present invention include ascorbic acid or salts thereof and ascorbic acid derivatives or salts thereof.

Ascorbic acid or the salts thereof include L-ascorbic acid or alkali metal salts thereof such as sodium L-ascorbate, potassium L-ascorbate and the like and alkali earth metal salts thereof such as calcium L-ascorbate and the like.

Among them, L-ascorbic acid or sodium L-ascorbate is particularly preferred.

The ascorbic acid derivatives include 2-glucoside ascorbate, phosphoric acid ascorbate, palmitic acid ascorbate, stearic acid ascorbate or salts thereof and the like.

The ascorbic acids or the salts thereof are widely used in the form of a powder, a granulated product or a crystal in the applications of medicines and foods, and they can safely be used.

In addition to the ascorbic acids or the salts thereof, sulfuric acid or salts thereof can be used in combination, and in this case, the SAMe-containing composition which is excellent in a storage stability can be obtained as well.

Sulfuric acid or the salts thereof are added so that an amount ratio thereof to SAMe contained in the SAMe-containing composition obtained is 0.1 to 3 time mole, preferably 1.5 to 2 time mole.

If the mount ratio to SAMe is less than 0.1 time mole, the SAMe-containing composition obtained is reduced in a storage stability. On the other hand, if the mount ratio exceeds 3 time mole, not only it does not provide more combined effect to the storage stability and is used in vain, but also the SAMe-containing composition obtained is reduced in a purity. Accordingly, both are not preferred.

On the other hand, the SAMe-containing composition which is excellent in a storage stability can be obtained as well by adding p-toluenesulfonic acid or salts thereof in addition to the ascorbic acids or the salts thereof.

p-Toluenesulfonic acid or the salts thereof are added so that an amount ratio thereof to SAMe contained in the SAMe-containing composition obtained from the SAMe-containing composition liquid is 0.1 to 2 time mole, preferably 0.5 to 1.5 time mole.

If the mount ratio to SAMe is less than 0.1 time mole, the SAMe-containing composition obtained is reduced in a storage stability. On the other hand, if the mount ratio exceeds 2 time mole, not only it does not provide more combined effect to the storage stability and is used in vain, but also the SAMe-containing composition obtained is reduced in a purity. Accordingly, both are not preferred.

Further, the SAMe-containing composition which is more excellent in a storage stability can be obtained by using sulfuric acid or the salts thereof and p-toluenesulfonic acid or the salts thereof in combination in addition to the ascorbic acids or the salts thereof.

An amount ratio of sulfuric acid or the salts thereof to SAMe contained in the SAMe-containing composition obtained after dried or subjected to crystallization treatment is 0.1 to 3 time mole, preferably 1.5 to 2.5 time mole, and an amount ratio of p-toluenesulfonic acid or the salts thereof to SAMe contained in the SAMe-containing composition obtained is 0.1 to 2 time mole, preferably 0.5 to 1.5 time mole.

Among them, more preferred is combination in which an amount ratio of sulfuric acid or the salts thereof to SAMe contained in the SAMe-containing composition obtained after dried and separated or crystallized is 2 time mole, in which an amount ratio of p-toluenesulfonic acid or the salts thereof is 1 time mole and in which an amount ratio of ascorbic acid or the salts thereof is 0.1 to 2 time mole, preferably 0.5 to 1.5 time mole.

As described above, the SAMe-containing composition which is far more excellent in a storage stability and which is reduced more in a use amount of p-toluenesulfonic acid or the salts thereof than SAMe having a conventional composition to which ascorbic acid or the salts thereof are not added can be obtained by adding sulfuric acid or the salts thereof, p-toluenesulfonic acid or the salts thereof and ascorbic acid or the salts thereof to the SAMe-containing composition liquid and then drying the above composition liquid or separating and drying a crystallized deposit obtained from the above composition liquid.

In addition to the additives described above, at least one kind of orally ingestible substances selected from halogen acids such as hydrobromic acid, hydroiodic acid and the like, mineral acids such as hydrochloric acid, phosphoric acid and the like, sulfonic acids such as 1,4-butanesulfonic acid and the like and salts thereof is not prevented from being added.

In order to obtain the SAMe-containing composition of the present invention, used are a method in which a solvent is removed from the composition liquid containing SAMe by distillation to dry up the composition and a method in which an organic solvent is added to the composition liquid containing SAMe or the condensate thereof to crystallize, separate and dry the SAMe-containing composition.

The drying method includes, for example, a spray drying method carried out by a spray dryer, a freeze-drying method, a decompression vacuum drying method and the like.

When the method in which the composition is crystallized and separated is used, a poor solvent to the composition comprising SAMe, sulfuric acid, p-toluenesulfonic acid and ascorbic acid, for example, ethanol, diethyl ether or the like is added to thereby crystallize the composition, and the crystal of the SAMe-containing composition can be obtained by a separating means such as filtration, centrifugal separation and the like.

The SAMe-containing composition of the present invention is a crystal or a crystalline powder, and from the viewpoint of the storage stability, the water content is controlled preferably to 1.5 mass % or less as is the case with a conventional product to which ascorbic acids or salts thereof are not added.

The SAMe-containing composition thus obtained shows a notably excellent storage stability on the acceleration conditions of, for example, 40° C. and RH 75% as compared with conventional SAMe-containing compositions.

Also, the SAMe-containing composition of the present invention can be compressed and tableted to prepare a tablet-shaped composition after adding, if necessary, additives such as other physiologically active components, a filler and the like. Further, the surface thereof can be coated, and the powdery composition can be turned into granules or the granules can be filled into capsules.

EXAMPLES

The present invention shall be explained below in further details with reference to examples and comparative examples, but the present invention shall not be restricted by these examples.

Quantitative analysis of SAMe in the present invention was carried out by liquid chromatography according to the conditions of the patent documents 4 and 5 described above.

The analysis was carried out on the chromatographic conditions of a column: GL Science Inc. GL-PACK PARTISIL-10 SCX 4.6×250 mm, an eluent: a 0.5M ammonium formate buffer solution (pH 4), a flow rate of 1.0 ml/minute, a detector: UV (254 nm) and a SAMe retention time of about 400 seconds.

Example 1

1-1 to 1-6

(a) Culture of Yeast Fungus

Yeast *saccharomyces cerevisiae* IFO2346 belonging to a *saccharomyces* genus was inoculated on 20 kg of an L-methionine-containing culture medium according to the culture method of the Non-patent documents 1, 2 and 8 described above, and it was aerobically cultured at a culture temperature of 27 to 29° C. for 6 days while aerating and stirring.

As a result thereof, a yeast fungus culture liquid 18 kg having a fungus concentration of 3.5 mass %, a SAMe content of 205 mg/g-dry yeast was obtained.

(b) Harvest of Yeast Fungus

The yeast fungus culture liquid 18 kg described above was treated by means of a continuous rotary centrifugal separator (HIMAC CENTRIFUGE CR10B2, manufactured by Hitachi, Ltd.) to obtain 3.49 kg of a yeast fungus concentrate having a concentration of 18 mass % in terms of a dry matter.

(c) Extraction of SAMe

Ethyl acetate 0.35 kg and distilled water 0.35 kg were added to 3.49 kg of the yeast fungus concentrate described above to carry out extraction at room temperature for 2.5 hours under stirring.

The above fungus extract was treated by the centrifugal separator described above using a sealing type centrifuge tube, and distilled water was further added to the separated enzyme residue to disperse it again. Then, the same centrifugal separating operation was carried out to thereby obtain 6.36 kg of the SAMe extract in total.

(d) Refining of SAMe Extract

The extract obtained in (c) described above was allowed to pass through a column filled with 3.5 L of Amberlite IRC-76 (weak acid ion exchange resin) to absorb SAMe once on the resin.

Then, 5.3 L of a 0.00005 mol/l (0.0001N) sulfuric acid aqueous solution was allowed to pass through the above column to wash it, and then the SAMe fraction was eluted with 12 L of a 0.2 mol/l (0.4N) sulfuric acid aqueous solution to obtain 12.5 L of a SAMe eluted fraction.

The above eluted fraction was allowed to further pass through a column filled with 3.5 L of Amberlite XAD-4 (synthetic absorbent) to thereby absorb impurities to obtain 12.5 kg of a refined SAMe-containing aqueous solution.

(e) Desalting of SAMe-Containing Aqueous Solution

The SAMe-containing aqueous solution obtained in (d) described above was allowed to pass through a column filled with 2.8 L of Amberlite IRC-67 (weak basic ion exchange resin) to obtain 16 kg of a composition liquid containing SAMe from which excess sulfuric acid ions were removed.

Sulfuric acid was present in a mole ratio of 1 (SAMe):2 (Sulfuric acid) to SAMe in the above SAMe-containing composition liquid.

(f) Addition of p-toluenesulfonic Acid to the SAMe-Containing Composition Liquid One time mole of p-toluenesulfonic acid was added to the SAMe-containing composition liquid obtained in (e) described above, and it was dissolved by stirring at room temperature for 30 minutes.

The solution thus obtained was concentrated under reduced pressure by means of an evaporator to obtain 950 g of the SAMe-containing composition liquid.

(g) Addition of Ascorbic Acid to the SAMe-Containing Composition Liquid

The SAMe-containing composition liquid 950 g obtained in (f) described above was transferred into a 3 L flask, and sodium L-ascorbate was added thereto in 0.2, 0.6, 1.0, 1.4, 1.8 and 2 time moles based on SAMe and dissolved by stirring at room temperature for 30 minutes.

(h) Drying

Each of the SAMe-containing composition liquids 1 kg having different addition amounts of sodium L-ascorbate was put in a glass tray for freeze drying of a freeze dryer (manufactured by ULVAC, Inc.) and frozen at −50° C., and then it was freeze-dried (ultimate vacuum degree: 13.33 Pa (0.1 Torr)) on the conditions of a final shelf temperature of 25° C. and 36 hours so that a moisture content after drying was 1.5 mass % or less.

Shown in Table 1 are the masses of the SAMe-containing compositions thus obtained, the mole ratios of the components thereof, the results of a storage stability test (residual ratio of SAMe) of the SAMe-containing compositions which was carried out on the conditions of 40° C. and RH 75% in a closed glass vessel and the results of a functional test (presence of unpleasant odor after 75 days passed since finishing the acceleration test).

The residual ratio of SAMe was determined by a quantitative method using the liquid chromatography described above, and the presence of odor after the storage stability test was determined by the functional test carried out by five panelists.

Example 2

2-1 to 2-6

Freeze-dried SAMe-containing compositions were obtained by treating in the same manner as in Example 1, except that p-toluenesulfonic acid was not added in the operation of (f) of Example 1.

Shown in Table 2 are the masses of the SAMe-containing compositions thus obtained, the mole ratios of the components thereof, the results of the storage stability test (residual ratio of SAMe) of the SAMe-containing compositions which was carried out on the accelerated conditions of 40° C. and RH 75% in a closed glass vessel and the results of the functional test (presence of unpleasant odor after 75 days passed since finishing the acceleration test).

Comparative Example 1

A freeze-dried SAMe-containing composition was obtained by treating in the same manner as in Example 1, except that sodium L-ascorbate was not added in the operation of (g) of Example 1.

A component mole ratio in the SAMe-containing composition thus obtained was SAMe:sulfuric acid:p-toluenesulfonic acid=1:2:1.

Shown in Table 1 are a mass of the SAMe-containing composition obtained, the mole ratios of the components thereof, the result of the storage stability test (residual ratio of SAMe) of the SAMe-containing composition which was carried out on the accelerated conditions of 40° C. and RH 75% in a closed glass vessel and the result of the functional test (presence of unpleasant odor after 75 days passed since finishing the acceleration test).

Comparative Example 2

A freeze-dried SAMe-containing composition 142 g was obtained by treating in the same manner as in Example 2, except that sodium L-ascorbate was not added.

A component mole ratio in the SAMe-containing composition thus obtained was SAMe:sulfuric acid=1:2.

Shown in Table 2 are a mass of the SAMe-containing composition obtained, the mole ratios of the components thereof, the result of the storage stability test (residual ratio of SAMe) of the SAMe-containing composition which was carried out on the conditions of 40° C. and RH 75% in a closed glass vessel and the result of the functional test (presence of unpleasant odor after 75 days passed since finishing the acceleration test).

Comparative Example 3

3-1 to 3-2

The operations of (a) to (f) were carried out in the same manner as in Example 1 to obtain 950 g of a SAMe-containing composition liquid.

The above liquid was put as it was in a glass tray for freeze drying of a freeze dryer (manufactured by ULVAC, Inc.) and frozen at −50° C., and then it was freeze-dried (ultimate vacuum degree: 13.33 Pa (0.1 Torr)) for 36 hours on the condition of a final shelf temperature of 25° C.

After freeze-dried, sodium L-ascorbate was added to the above SAMe-containing composition in an amount of 0.6 and 1.0 time moles based on SAMe, and they were stirred and mixed in a mortar at room temperature under nitrogen atmosphere.

Shown in Table 3 are the masses of the SAMe-containing compositions obtained, the mole ratios of the components thereof, the results of the storage stability test (residual ratio of SAMe) of the SAMe-containing composition which was carried out on the conditions of 40° C. and RH 75% in a closed glass vessel and the results of the functional test (presence of unpleasant odor after 75 days passed since finishing the acceleration test).

Comparative Example 4

4-1 to 4-2

SAMe-containing compositions were obtained by treating in the same manner as in Comparative Example 3, except that p-toluenesulfonic acid was not added in the operation of (f).

Shown in Table 3 are the masses of the SAMe-containing compositions thus obtained, the mole ratios of the components thereof, the results of the storage stability test (residual ratio of SAMe) of the SAMe-containing compositions which was carried out on the accelerated conditions of 40° C. and RH 75% in a closed glass vessel and the results of the functional test (presence of unpleasant odor after 75 days passed since finishing the acceleration test).

Table 1 results of the storage stability test of the SAMe-containing compositions which was carried out on the accelerated conditions of 40° C. and RH 75% in a closed glass vessel (SAMe-containing compositions containing p-toluenesulfonic acid)

| | Mole ratio of the components in the SAMe-containing composition*1 | Mass (g) of SAMe-containing composition | SAMe residual ratio (%) in the SAMe-containing composition Elapsed days | | | | | Presence of unpleasant odor after 75 days passed since finishing acceleration test*2 |
|---|---|---|---|---|---|---|---|---|
| | | | After 10 days | After 40 days | After 45 days | After 60 days | After 75 days | |
| Example 1-1 | 1:2:1:0.2 | 192 | 100 | 100 | 97.6 | 99.7 | 97.6 | A |
| Example 1-2 | 1:2:1:0.6 | 210 | 100 | 100 | 100 | 100 | 100 | A |
| Example 1-3 | 1:2:1:1 | 229 | 100 | 100 | 100 | 100 | 100 | A |
| Example 1-4 | 1:2:1:1.4 | 238 | 100 | 100 | 100 | 99.7 | 92.4 | A |
| Example 1-5 | 1:2:1:1.8 | 257 | 100 | 100 | 99.2 | 87.1 | 71.2 | B |
| Example 1-6 | 1:2:1:2 | 276 | 100 | 100 | 98.5 | 83.9 | 68.7 | B |
| Comparative Example 1 | 1:2:1:0 | 182 | 100 | 90.5 | 86.4 | 76.8 | 65.4 | B |

*1: mole ratio (SAMe:sulfuric acid:p-toluenesulfonic acid:sodium L-ascorbate) of the respective components contained in the SAMe-containing composition
*2: A: no unpleasant odor, B: slight unpleasant odor, C: unpleasant odor present Table 2 results of the storage stability test of the SAMe-containing compositions which was carried out on the accelerated conditions of 40° C. and RH 75% in a closed glass vessel (SAMe-containing compositions containing no p-toluenesulfonic acid)

| | Mole ratio of the components in the SAMe-containing composition*1 | Mass (g) of SAMe-containing composition | SAMe residual ratio (%) in the SAMe-containing composition Elapsed days | | | | | Presence of unpleasant odor after 75 days passed since finishing acceleration test*2 |
|---|---|---|---|---|---|---|---|---|
| | | | After 10 days | After 40 days | After 45 days | After 60 days | After 75 days | |
| Example 2-1 | 1:2:0:0.2 | 151 | 100 | 100 | 94.3 | 88.7 | 78.4 | B |
| Example 2-2 | 1:2:0:0.6 | 169 | 100 | 100 | 97.6 | 93.4 | 88.4 | A |
| Example 2-3 | 1:2:0:1 | 182 | 100 | 100 | 98.6 | 97.2 | 95.6 | A |

-continued

|  | Mole ratio of the components in the SAMe-containing composition*1 | Mass (g) of SAMe-containing composition | SAMe residual ratio (%) in the SAMe-containing composition Elapsed days | | | | | Presence of unpleasant odor after 75 days passed since finishing acceleration test*2 |
|---|---|---|---|---|---|---|---|---|
|  |  |  | After 10 days | After 40 days | After 45 days | After 60 days | After 75 days |  |
| Example 2-4 | 1:2:0:1.4 | 198 | 100 | 100 | 97.8 | 80.1 | 72.4 | B |
| Example 2-5 | 1:2:0:1.8 | 217 | 100 | 100 | 90.1 | 79.5 | 68.7 | B |
| Example 2-6 | 1:2:0:2 | 235 | 100 | 100 | 85.6 | 77.8 | 68.1 | B |
| Comparative Example 1 | 1:2:0:0 | 142 | 100 | 87.9 | 80.6 | 70.2 | 53.4 | C |

*1: mole ratio (SAMe:sulfuric acid:p-toluenesulfonic acid:sodium L-ascorbate) of the respective components contained in the SAMe-containing composition
*2: A: no unpleasant odor, B: slight unpleasant odor, C: unpleasant odor present Table 3 results of the storage stability test of the SAMe-containing compositions which was carried out on the accelerated conditions of 40° C. and RH 75% in a closed glass vessel (comparison of a case in which sodium L-ascorbate was added before freeze-drying with a case in which it was added after freeze-drying)

|  | Mole ratio of the components in the SAMe-containing composition*1 | Mass (g) of SAMe-containing composition | SAMe residual ratio (%) in the SAMe-containing composition Elapsed days | | | | | Presence of unpleasant odor after 75 days passed since finishing acceleration test*2 |
|---|---|---|---|---|---|---|---|---|
|  |  |  | After 10 days | After 40 days | After 45 days | After 60 days | After 75 days |  |
| Example 1-2 | 1:2:1:0.6 | 210 | 100 | 100 | 100 | 100 | 100 | A |
| Example 1-3 | 1:2:1:1 | 229 | 100 | 100 | 100 | 100 | 100 | A |
| Example 3-1 | 1:2:1:0.6 | 213 | 100 | 89.4 | 85.7 | 74.9 | 63.7 | B |
| Example 3-2 | 1:2:1:1 | 234 | 100 | 89.9 | 86.3 | 75.6 | 64.2 | B |
| Example 2-2 | 1:2:0:0.6 | 169 | 100 | 100 | 97.6 | 93.4 | 88.4 | A |
| Example 2-3 | 1:2:0:1 | 182 | 100 | 100 | 98.6 | 97.2 | 95.6 | A |
| Comparative Example 4-1 | 1:2:1:0.6 | 170 | 100 | 84.2 | 78.1 | 69.6 | 51.3 | C |
| Comparative Example 4-2 | 1:2:1:1 | 185 | 100 | 84.8 | 78.3 | 68.9 | 52.1 | C |

*1: mole ratio (SAMe:sulfuric acid:p-toluenesulfonic acid:sodium L-ascorbate) of the respective components contained in the SAMe-containing composition
*2: Examples 1 and 2: sodium L-ascorbate was added before freeze-drying Comparative Examples 3 and 4: sodium L-ascorbate was added after freeze-drying
*3: A: no unpleasant odor, B: slight unpleasant odor, C: unpleasant odor present Industrial Applicability According to the present invention, at least ascorbic acids or salts thereof are added to a composition liquid containing SAMe and, if necessary, stirred and dissolved, and then the above composition liquid is dried or a crystallized deposit obtained from the above composition liquid is separated and dried, whereby a SAMe-containing composition which is very excellent in a storage stability can be produced and provided.

Also, addition of the ascorbic acids or the salts thereof according to the present invention makes it possible to reduce an addition amount of p-toluenesulfonic acid.

Further, a rise in the storage stability makes it possible to prevent sulfurous smell brought about by decomposition from being generate to improve easiness of ingestion to a large extent.

What is claimed is:

1. A production process for a S-adenosyl-L-methionine-containing composition, comprising adding sulfuric acid or a salt thereof, p-toluenesulfonic acid or a salt thereof and sodium L-ascorbate to a composition liquid containing S-adenosyl-L-methionine, and then drying the above composition liquid or separating and drying a crystallized deposit obtained from the above composition liquid, wherein an amount ratio of sodium L-ascorbate to S-adenosyl-L-methionine contained in the S-adenosyl-L-methionine-containing composition obtained falls in a range of 0.2 to 1.4 times mole.

2. The production process for a S-adenosyl-L-methionine-containing composition as described in claim 1, wherein an amount ratio of sulfuric acid or the salt thereof to S-adenosyl-L-methionine contained in the S-adenosyl-L-methionine-containing composition obtained falls in a range of 0.1 to 3 times mole.

3. The production process for a S-adenosyl-L-methionine-containing composition as described in claim 1, wherein an amount ratio of p-toluenesulfonic acid or the salt thereof to S-adenosyl-L-methionine contained in the S-adenosyl-L-methionine-containing composition obtained falls in a range of 0.1 to 2 times mole.

4. The production process for a S-adenosyl-L-methionine-containing composition as described in claim 1, wherein said composition liquid has a pH of 1 to 5.

5. A process for producing a stable S-adenosyl-L-methionine-containing composition, comprising adding sulfuric acid or a salt thereof, p-toluenesulfonic acid or a salt thereof and sodium L-ascorbate to a composition liquid containing S-adenosyl-L-methionine, and then drying the above composition liquid or separating and drying a crystallized deposit obtained from the above composition liquid, the stable S-adenosyl-L-methionine-containing composition being stable under accelerating conditions of 40° C. and a relative humidity of 75%, and wherein an amount ratio of sodium L-ascorbate to S-adenosyl-L-methionine contained in the S-adenosyl-L-methionine-containing composition obtained falls in a range of 0.2 to 1.4 times mole.

* * * * *